(12) United States Patent
Raudins

(10) Patent No.: US 11,182,911 B2
(45) Date of Patent: *Nov. 23, 2021

(54) ULTRASOUND-BASED GEOMETRY DETERMINATION FOR ELECTROPHYSIOLOGICAL MAPPING

(71) Applicant: CARDIOINSIGHT TECHNOLOGIES, INC., Independence, OH (US)

(72) Inventor: Glenn D. Raudins, Chagrin Falls, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 28 days.

This patent is subject to a terminal disclaimer.

(21) Appl. No.: 16/874,298

(22) Filed: May 14, 2020

(65) Prior Publication Data

US 2020/0273182 A1    Aug. 27, 2020

Related U.S. Application Data

(63) Continuation of application No. 15/991,478, filed on May 29, 2018, now Pat. No. 10,713,800.

(Continued)

(51) Int. Cl.
*G06T 7/20* (2017.01)
*G06T 7/292* (2017.01)
(Continued)

(52) U.S. Cl.
CPC ............ *G06T 7/292* (2017.01); *A61B 5/0035* (2013.01); *A61B 5/0044* (2013.01); *A61B 5/061* (2013.01);
(Continued)

(58) Field of Classification Search
CPC .. G06T 7/292; G06T 7/12; G06T 7/62; G06T 7/10; G06T 7/30; G06T 2207/10136; G06T 2207/30048; A61B 5/282; A61B 5/061; A61B 5/0035; A61B 8/4245; A61B 5/0044; A61B 8/5223; A61B 5/7285; A61B 8/0841; A61B 5/6823; A61B 8/5253;
(Continued)

(56) References Cited

U.S. PATENT DOCUMENTS

2009/0177071 A1    7/2009 Doron et al.
2011/0190629 A1    8/2011 Matthias et al.
(Continued)

OTHER PUBLICATIONS

Applicant: CardioInsight Technologies, Inc.; International Search Report and PCT Written Opinion; Autorized Officer Yeonkyung Kim; Date of Completion: Sep. 10, 2018; 14 pgs.

*Primary Examiner* — Qian Yang
(74) *Attorney, Agent, or Firm* — Tarolli, Sundheim, Covell & Tummio LLP

(57) ABSTRACT

Systems and methods can be used for ultrasound-based geometry determination for cardiac mapping. A patient can be scanned with an ultrasound while wearing body surface electrodes. While the scanning takes place, the location of the ultrasound transducer can be tracked in three-dimensional space. The electrodes can be tracked and located in the same coordinate system as the image volume. Therefore, each electrode's location can be determined relative to the acquired image volume such that corresponding geometry data is generated for the heart and the electrodes.

20 Claims, 6 Drawing Sheets

Related U.S. Application Data

(60) Provisional application No. 62/511,665, filed on May 26, 2017.

(51) Int. Cl.

| | | |
|---|---|---|
| *A61B 5/06* | (2006.01) | |
| *A61B 5/00* | (2006.01) | |
| *A61B 8/00* | (2006.01) | |
| *A61B 8/08* | (2006.01) | |
| *G06T 7/12* | (2017.01) | |
| *A61B 5/282* | (2021.01) | |
| *G06T 7/62* | (2017.01) | |
| *G06T 7/10* | (2017.01) | |
| *G06T 7/30* | (2017.01) | |
| *A61N 1/18* | (2006.01) | |
| *A61N 1/00* | (2006.01) | |
| *A61N 1/05* | (2006.01) | |

(52) U.S. Cl.
CPC ............ *A61B 5/282* (2021.01); *A61B 5/6823* (2013.01); *A61B 5/7285* (2013.01); *A61B 8/0841* (2013.01); *A61B 8/4245* (2013.01); *A61B 8/5223* (2013.01); *G06T 7/10* (2017.01); *G06T 7/12* (2017.01); *G06T 7/30* (2017.01); *G06T 7/62* (2017.01); *A61B 8/5253* (2013.01); *A61B 8/543* (2013.01); *A61B 2562/0204* (2013.01); *A61B 2562/046* (2013.01); *A61N 1/00* (2013.01); *A61N 1/056* (2013.01); *A61N 1/0587* (2013.01); *A61N 1/18* (2013.01); *G06T 2207/10136* (2013.01); *G06T 2207/30048* (2013.01)

(58) Field of Classification Search
CPC .............. A61B 2562/046; A61B 8/543; A61B 2562/0204; A61N 1/18; A61N 1/00; A61N 1/0587; A61N 1/056; G16H 50/30
See application file for complete search history.

(56) References Cited

U.S. PATENT DOCUMENTS

| | | |
|---|---|---|
| 2016/0089057 A1 | 3/2016 | Ping et al. |
| 2016/0192902 A1 | 7/2016 | Werneth et al. |
| 2016/0225140 A1 | 8/2016 | Jo |
| 2016/0338611 A1 | 11/2016 | Alexander et al. |
| 2017/0238905 A1 | 8/2017 | Villain |

ULTRASOUND-BASED GEOMETRY DETERMINATION FOR ELECTROPHYSIOLOGICAL MAPPING

CROSS REFERENCE TO RELATED APPLICATION

This application is a Continuation of U.S. patent application Ser. No. 15/991,478, filed May 29, 2018, which claims the benefit of U.S. Provisional Patent Application No. 62/511,665, filed May 26, 2017, and entitled ULTRASOUND-BASED GEOMETRY DETERMINATION FOR ELECTROPHYSIOLOGICAL MAPPING, which is incorporated herein by reference in its entirety.

TECHNICAL FIELD

This disclosure relates to ultrasound-based geometry determination for electrophysiological mapping.

BACKGROUND

Advanced cardiac mapping can occur based on a combination of a computed tomography (CT) scan and signals recorded by body surface electrodes. The CT scan can be used to acquire both the epicardial surface of the heart and the location of the body surface electrodes in relation to the epicardial surface. However, the CT scan is expensive and CT machines are not readily available in some facilities. Additionally, the CT scan exposes the patient to a large amount of unnecessary radiation.

SUMMARY

In one example, a method includes receiving, by a system comprising a processor, ultrasound image data as an ultrasound transducer scans a patient's body that includes a plurality of body surface electrodes at positions distributed across the body surface. The ultrasound image data includes at least one ultrasound image of the patient's heart. The method also includes receiving, by the system, tracking data from at least one tracking sensor associated with the ultrasound transducer. The tracking data represents locations of the ultrasound transducer in three dimensional space as an ultrasound transducer scans the patient's body. The method also includes determining, by the system, cardiac surface data to represent locations along a surface of the patient's heart based on the tracking data and the ultrasound image data. The method also includes deriving, by the system, geometry data representing a geometric relationship between the locations of the plurality of body surface electrodes and locations along the surface of the patient's heart represented by the cardiac surface data.

In another example, a system includes a plurality of body surface electrodes positioned at relative positions and configured to be placed on a body surface of a patient to measure electrical activity non-invasively from the body surface. A non-transitory memory can store data and instructions and a processor can access the non-transitory memory and execute the instructions to access ultrasound image data corresponding to one or more ultrasound transducer scans of a patient's body. The ultrasound image data includes at least one ultrasound image frame that includes the patient's heart. The instructions are further to access tracking data representing a position of at least one tracking sensor associated with the ultrasound transducer. The tracking data represents locations of the ultrasound transducer in three dimensional space as the ultrasound transducer scans the patient's body. The instructions are further to determine cardiac surface data to represent locations along a surface of the patient's heart based on the tracking data and the ultrasound image data. The instructions are further to derive geometry data representing a geometric relationship between the position of the plurality of body surface electrodes and the locations along the surface of the patient's heart represented by the cardiac surface data.

DETAILED DESCRIPTION

Figure 1:
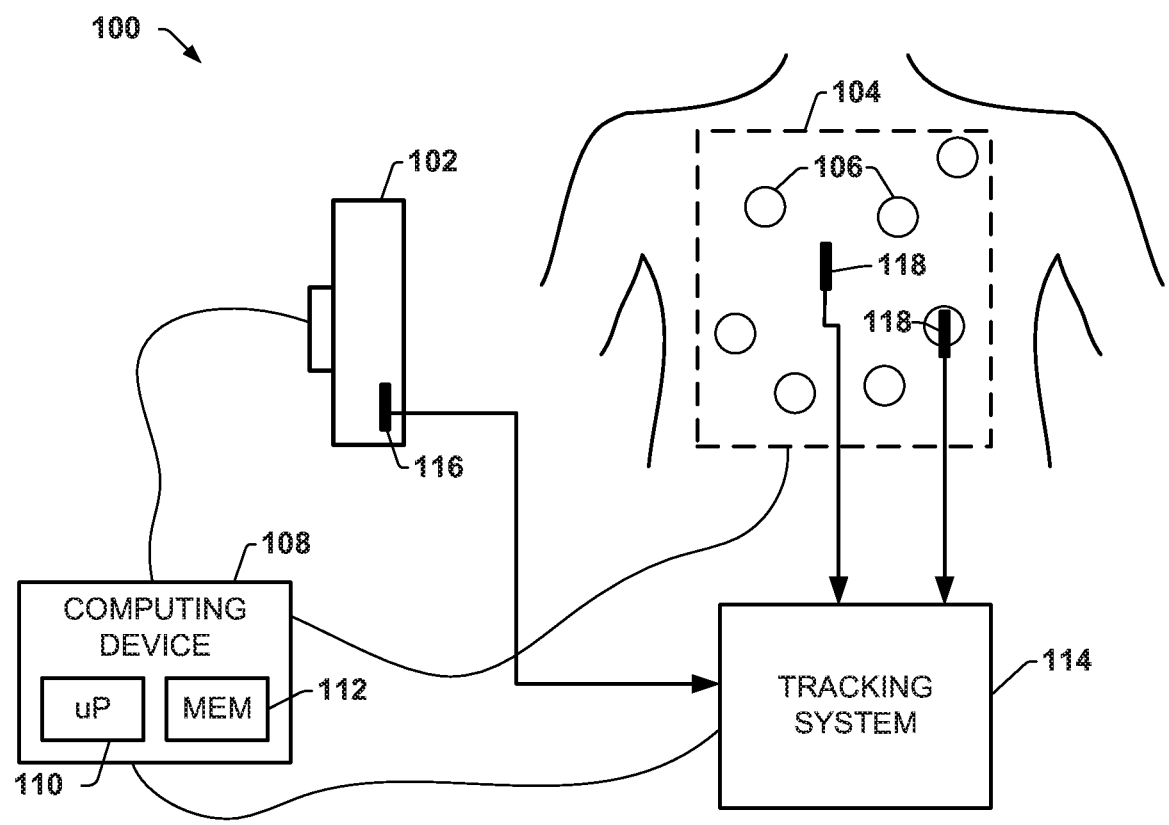
FIG. 1 depicts an example of a system for ultrasound-based geometry determination for cardiac mapping.

This disclosure relates to determining geometry data representing geometric relationship between a cardiac surface and body surface electrodes. The geometry data may be used in performing electrophysiological image mapping (e.g., electrocardiographic imaging (ECGI)).

As an example, ultrasound image data is acquired via an ultrasound transducer having a position that is tracked during ultrasound scanning of the patient's body, including the patient's heart. The position tracking may be implemented by an ultrasound tracking sensor attached to the ultrasound transducer, where the sensor position in three-dimensional space is tracked by a tracking system. The tracking system thus can generate tracking data that is stored (e.g., in memory) to represent the position of ultrasound transducer) for each image frame. The geometry of a cardiac surface (e.g., a plurality of locations distributed across the cardiac surface) can be determined from the ultrasound image data and the tracking data.

The locations of body surface electrodes are also determined, which may be based on tracking data provided by the tracking system or otherwise. For example, a plurality of electrode tracking sensors can be provided at locations known relative to body surface electrodes. Thus, by knowing the location of the electrode tracking sensors in three-dimensional (3D) space (e.g., from tracking data), the location of the body surface electrodes, which have a known relative position with respect to each other, is determined in 3D space. Because of such electrode spatial tracking, expensive and time consuming imaging, as is done in many existing electrocardiographic mapping systems, can be omitted from the clinical workflow-saving time and reducing costs. Once the location of the location of the body surface electrodes and the cardiac surface are known, the geometry data can be readily determined to represent the geometric relationship between the cardiac surface (epicardial and/or endocardial) and the body surface electrodes in a common 3D coordinate system. The geometric relationship may be provided in a variety of forms, such as 3D spatial coordinates and/or vectors between such coordinates.

In some examples, a plurality of two-dimensional (2D) or three-dimensional (3D) ultrasound images are correlated and compounded together to create an ultrasound image (e.g., a volume or image set) of at least a portion of the heart. For example, the ultrasound beam is emitted from the transducer oriented at a plurality of different angles to acquire several overlapping scans of the patient's thorax, including the heart, to generate corresponding images of the patient's thorax from different viewing angles. The images can be spatially compounded to construct an ultrasound image set (e.g., image volume) of at least the portion of one or more cardiac surfaces (epicardial and/or endocardial). The compounding combines a number of ultrasound images of a given target that have been obtained from multiple angles into a single compounded image by combining the data received from each point in the compound image target which has been received from each angle. To form the compounded image volume, the component frames or target echoes to be combined are spatially aligned (if not already aligned by a common beam steering reference) by scan conversion or resampling. The common spatial locations in the image field are then compounded, such as by averaging or summing and the resultant compound image is stored in image data and can be displayed.

To facilitate accurate compounding and enable localizing the cardiac surface, a tracking sensor is fixed with respect to the housing of the ultrasound transducer to track its position (e.g., in three-dimensional space) during recording of the ultrasound images. For example, the tracking sensor can track both position and orientation of the transducer to further facilitate compounding of ultrasound images. Additionally, the locations of the body surface electrodes can be tracked (e.g., by one or more electrode tracking sensors) in a three-dimensional coordinate system, which may be a common spatial coordinate system for geometry of the cardiac surface. For example, the common coordinate system can be a tracking coordinate system of a tracking system or an ultrasound coordinate system of the ultrasound imaging system. The position of tracking sensors of the ultrasound transducer and/or the body surface electrodes can be based on a tracking system (e.g., magnetic tracking, optical tracking, electromagnetic tracking, etc.), which may be the same tracking system or separate tracking systems.

By way of further example, in some existing approaches, the geometry data for cardiac mapping is determined using computed tomography (CT) imaging. However, CT imaging is expensive, is not widely available in some areas, and exposes the patient to ionizing radiation. Using ultrasound, as disclosed herein, can reduce costs, increase the availability of the electrophysiological mapping regardless of the availability of CT imaging, and can reduce or eliminate the radiation exposure for the patient. For example, since ultrasound imaging systems are widely available, the approach disclosed herein does not require coordination with a radiology department (costs time and requires transfer of the images when completed). In the end the clinical workflow for electrophysiological image mapping can be greatly simplified, making it more accessible to caregivers and patients throughout the world.

FIG. 1 illustrates an example system 100 for ultrasound-based geometry determination, such as for use in electrocardiographic mapping. As disclosed herein, the cardiac geometry data can be used in combination with measured electrical data (non-invasive electrical measurements) to determine an electroanatomic map for an internal body structure, such as the heart or brain. For sake of consistency, the following disclosure describes the electroanatomic map and electrical measurements as corresponding to the heart. In other examples, maps could be determined for other anatomic structures, such as the brain.

The system 100 can include an ultrasound system, including an ultrasound transducer 102, to acquire a plurality of ultrasound images (e.g., image frames). For example, a plurality of image frames may be acquired by positioning the transducer at different angles and compounded to provide a 3D image of the patient's heart. Additionally or alternatively, an electron beam may be used to steer the beam to acquire images at different angles through the body surface.

The ultrasound transducer 102 can acquire ultrasound images of at least a portion of the heart, including one or more surfaces thereof (e.g., epicardial and/or endocardial surfaces). The ultrasound transducer 102 can be a standard ultrasound transducer that can acquire ultrasound images of the heart. For example, the ultrasound transducer 102 can be used in connection with a gated freehand system to acquire 2D (b-mode) ultrasound images and/or 3D ultrasound images.

By way of example, the acquisition of ultrasound images may be gated to the cardiac cycle. Such gating can be performed via ECG signal or image based retrospective gating techniques. In some examples, the acquisition may be gated in response to cardiac electrical signals (e.g., electrograms) from one or more body surface electrodes 106. That is, since the ultrasound images can be acquired over time (according to an imaging sample rate) and cardiac electrical activity can be measured concurrently, one or more image sets may be gated to the cardiac electrical cycle. The gating process provides the ability to either select a single phase of the heart to image and segment and, in turn, provide a corresponding surface model. In another example, multiple phases of the heart could be selected over a series of cycles and the images for each cycle segmented and compounded to provide a plurality of cardiac surface models for different respective phases of the cardiac cycle. With multiple phases of the heart modeled, and real-time vest electrode tracking, data from the electrodes could be mapped to appropriate phase model. This amounts to a multi-phase heart model with mapped data.

The system 100 also includes an electrical measurement system to acquire electrical data (e.g., body surface electrical potentials, such as unipolar electrograms) from a sensor array 104. The sensor array 104 that includes a plurality of electrodes 106 configured to be placed on an outer surface of a patient's torso, such as the thorax. The sensor array 104 is positioned external to the patient's body to acquire cardiac electrical data non-invasively, rather than invasively (e.g., using a catheter or other device to bring the electrodes 106 into contact with or near the heart itself). Although one side of the patient's body is shown in FIG. 1, the electrodes 106 can be distributed across the front and back of the patient's thorax. Additionally, while eight electrodes are shown in the example of FIG. 1, a greater or fewer number of electrodes can be used, in different orientations, depending on the application needs.

For example, to acquire desired data for body surface mapping or electrocardiographic imaging (ECGI), a vest or other structure can be applied to the patient's thorax as to completely cover the patient's torso with a generally evenly distributed arrangement of a plurality of electrodes (e.g., greater than 100, such as about 252 electrodes). A relative position location and distribution of at least certain groups of the electrodes 106 in sensor array 104 known a priori and stored in memory (e.g., of a computing system 108). For example, the electrodes 106 may be coupled to one or more substrates, such as a web of flexible material that may be in the form of a wearable garment (e.g., a vest) or otherwise configured to be attached to the patient's torso. The substrate thus may constrain the relative position of electrodes 106 residing thereon. Some examples of a non-invasive sensor array that can be used as array 104 are shown and described in U.S. Pat. No. 9,655,561, and International application No. PCT/US2009/063803, each of which is incorporated herein by reference.

The ultrasound transducer 102 and the sensor array 104 can interface with one or more computing devices 108 (directly or through respective processing devices). For example, the computing device 108 can be a standalone computer (e.g., personal computer, laptop), a workstation, an application specific machine, or in a network environment in which one or more of the modules or data can reside locally or remotely relative to where a user interacts with the system 100 through one or more user input device and/or graphical user interfaces. The computing device 108 thus includes one or more processors 110 and memory 112. The processor 110 accesses data and executable instructions stored in the memory to perform functions and methods disclosed herein.

The system 100 also includes one or more tracking systems 114 configured to provide tracking data representing a position of at least one tracking modality (e.g., a tracking sensor) 116 that is associated with (e.g., mounted to) the ultrasound transducer 102. For example, the tracking sensor 116 is implemented as a coil that is part of (connected to provide a signal to) the tracking system 114 in response to an electromagnetic field generated by one or more field generators of the tracking system. The tracking system 114 thus can enable spatial tracking of each sensor and object to which it is attached in five or six degrees of freedom. Examples of sensors that can be detected by an electromagnetic type of tracking system are commercially available from Northern Digital, Inc., of Ontario, Canada. In other examples, other types of tracking modalities to ascertain (track) the 3D location of the ultrasound transducer 102 may be used depending on the type of tracking system 108, such as an optical tracking system, a magnetic tracking system, or other type of tracking system.

For the example of electromagnetic (EM) tracking, a sufficient number of EM magnetic sensors are integrated into the sensor array such that the general shape/location of the vest known or can be readily determined. The tracking sensors would provide 3D locations and orientation in the same coordinate system as the transducer due to the shared magnetic field that is used to provide the tracking data for both the transducer and the electrodes 106. In some examples, the number of sensors needed may be less than the number of electrodes, as it is easy enough to use orientation and location at sensors to interpolate the intermediate locations. In other examples, to reduce the number of computations, a tracking sensor may be integrated into each of the electrodes 106.

In an example of optical tracking, assuming the patient is lying down, one side of the sensor array would likely not be visible, meaning there is some unknown information. In other examples, the patient may be sitting or standing during the scanning and tracking of sensor locations. As yet another example, fiber optic tracking can be used as the optical tracking solution or as a replacement to the magnetic tracking for electrode tracking. For example, a fiber optic containing Fiber Bragg Grating sensors can detect the 3D position and shape along the fiber, at hundreds of locations. The sensor array 104 could have a single fiber wound through the vest, providing the relative shape of the vest along that fiber. These relative locations together with a general vest location, in the real world coordinate system, would provide sufficient location information of all of the electrodes in that coordinate system, which could be registered with the ultrasound image space.

The tracking system 114 provides the tracking data to the computing device 108 to represent locations of the ultrasound transducer 102 in 3D space (e.g., as coordinates in a 3D coordinate system of the tracking system 114) as the ultrasound transducer scans the patient's body. The tracking system 114 thus can provide the tracking data to the computing device 108 through a communications link (e.g., wired or wireless). The tracking data and ultrasound image data can be time synchronized (e.g., via time stamps) such that the location of the transducer at a given time can be linked (programmatically as a data record) with respective image data. Since the ultrasound image data includes an image of the heart surface(s) and the tracking data represents location of the transducer during scanning, the computing device is programmed to determine cardiac surface data representing locations along the surface of the patient's heart based on the tracking data and the ultrasound image data.

By way of example, the computing device 108 is programmed (e.g., processor 110 executes instructions) to segment the ultrasound image (e.g., spatially compounded image) to determine a plurality of spatial points distributed across the surface of the patient's heart. In an example, the patient's heart is segmented based on long and short axes of the patient's heart. In another example, the patient's heart is segmented based on an identification of one or more anatomical landmarks of the patient's heart, such as the atrioventricular groove, the pulmonary artery, the aortic arch, and/or the apex. The surface of the heart can be modeled as a cardiac surface mesh based on the segmenting, and the plurality of points distributed across the surface correspond to nodes of the surface mesh. Based on known operating characteristics and configuration of the ultrasound transducer 102 and the tracking data representing the position of the transducer 102 during scanning, the position of each of the points across the cardiac surface can be determined in 3D space (e.g., as coordinates).

In some examples, the segmentation may be performed in real time during ultrasound image acquisition (scanning) with the transducer 102. Segmentation can be done via automated algorithms (E.g. model based segmentation, neural network, etc.) or manually. Real time segmentation of ultrasound images allows for iterative improvement of segmentation information by acquiring more images. For example, spatial compounding and segmentation may be performed to generate a graphical representation of the cardiac surface, which can provide feedback (graphical information on a display) to help guide the user during scanning.

As a further example, a confidence metric may be computed by the computing device 108 as a function of how complete or incomplete the correlated and compounded ultrasound image of the patient's heart. A confidence metric can be derived from the number (e.g., a relative quantity) of ultrasound image planes that have contributed to individual voxels in the compounded voxel volume. For example, if only 60% of the voxels in a volume region have been sampled by ultrasound images, the confidence metric (~60%) is lower than an area where 90% of the voxels have recorded values. Additionally or alternatively, the number of times the individual voxel has been compounded by the ultrasound images can likewise be used to ascertain a measure of completeness for the scanned image volume. Multiple planes per voxel can help ensure the accuracy of the actual data stored at the voxel, and thereby the accuracy of the resulting segmentation. In this way, the confidence matrix can help identify areas that have too many missing voxels and the system can provide feedback to guide the user to further scan areas that have too many missing voxels and/or too few planes contributing to those voxels that do have data. Additionally, the segmentation can drive the regions of importance for reporting this metric to the user.

The feedback further may indicate what region(s) of the heart are needed to be scanned such that the user can reposition the transducer to scan the missing region(s). For example, segmentation may be implemented to identify the location of ends of the long and short axes of the heart. The confidence metric, for example, can be computed as an error function based on statistical analysis of the segmented compounded ultrasound image (e.g., edge detected via thresholding) to indicate a confidence value for the ends of the long and short axes. For example, an error associated with pixels or voxels corresponding to these or other points on cardiac surface can be computed to provide the confidence metric.

Additionally, the location of one or more of the electrodes 106 are known. In some examples, the locations are known in 3D space a priori or, in other examples, the locations can be determined based on one or more electrode spatial tracking modality 118. Similar to spatial tracking modality 116, for example, the sensor tracking modality 118 can be part of the tracking system 114. The tracking system 114 thus can provide the tracking data to the computing device 108 to represent the position of the ultrasound tracking sensor 116 and each of the electrode tracking sensors 118 over time. As mentioned, the tracking data can be time synchronized (using timestamps) with respect to the image data from the ultrasound transducer 102 and the electrical data sensed from the sensor array 104.

As an example, the position of at least a portion of the electrodes 106 also tracked, directly or indirectly, by use of an arrangement of the electrode tracking sensors 118 integrated into the sensor array 104. For example, a given electrode 106 is directly tracked where a sensor is co-located with (e.g., vertically aligned with a centroid or edge of the given electrode. A given electrode is indirectly tracked where a respective tracking sensor has a known position with respect to the given electrode. Thus by placing the tracking sensors 118 at locations distributed across the sensor array at known relative positions with respect to the electrodes, the electrode locations in 3D space are readily determined based on the tracking data that represents the locations of the tracking sensors. The locations of each of the electrodes in 3D space thus can be stored in the memory 112 as electrode location data.

In an example, the ultrasound transducer 102 and the sensor array 104 and tracking system 114 can interface with separate computing devices 108. As another example, the ultrasound transducer 102, the sensor system 104 and tracking system 114 can interface with the same computing device 108. The computing device 108 can also be configured control image acquisition and track the location of the ultrasound transducer 102 in three dimensions (3D) during image acquisition based on the tracking data from tracking system 114. The computing device 106 can also control data acquisition by the sensor array 104 and track location of the sensor system 104 based on tracking data from the tracking system 108. The computing device is further configured to derive geometry data representing a 3D geometric relationship between the position of the plurality of body surface electrodes 106 and the locations along the surface of the patient's heart, as represented by the cardiac surface data. As disclosed herein (see, e.g., FIGS. 4 and 5), electrical data measured by the electrodes can be stored in memory as electrical data and combined with the geometry data (determined by computing device based on ultrasound image data and tracking data) to generate one or more electrocardiographic maps. The use of ultrasound, rather than CT, to determine the geometry data can enable the cardiac mapping to occur in more varied environments, in combination with other traditional cardiac exams, in less time and at a lower cost.

Figure 2:
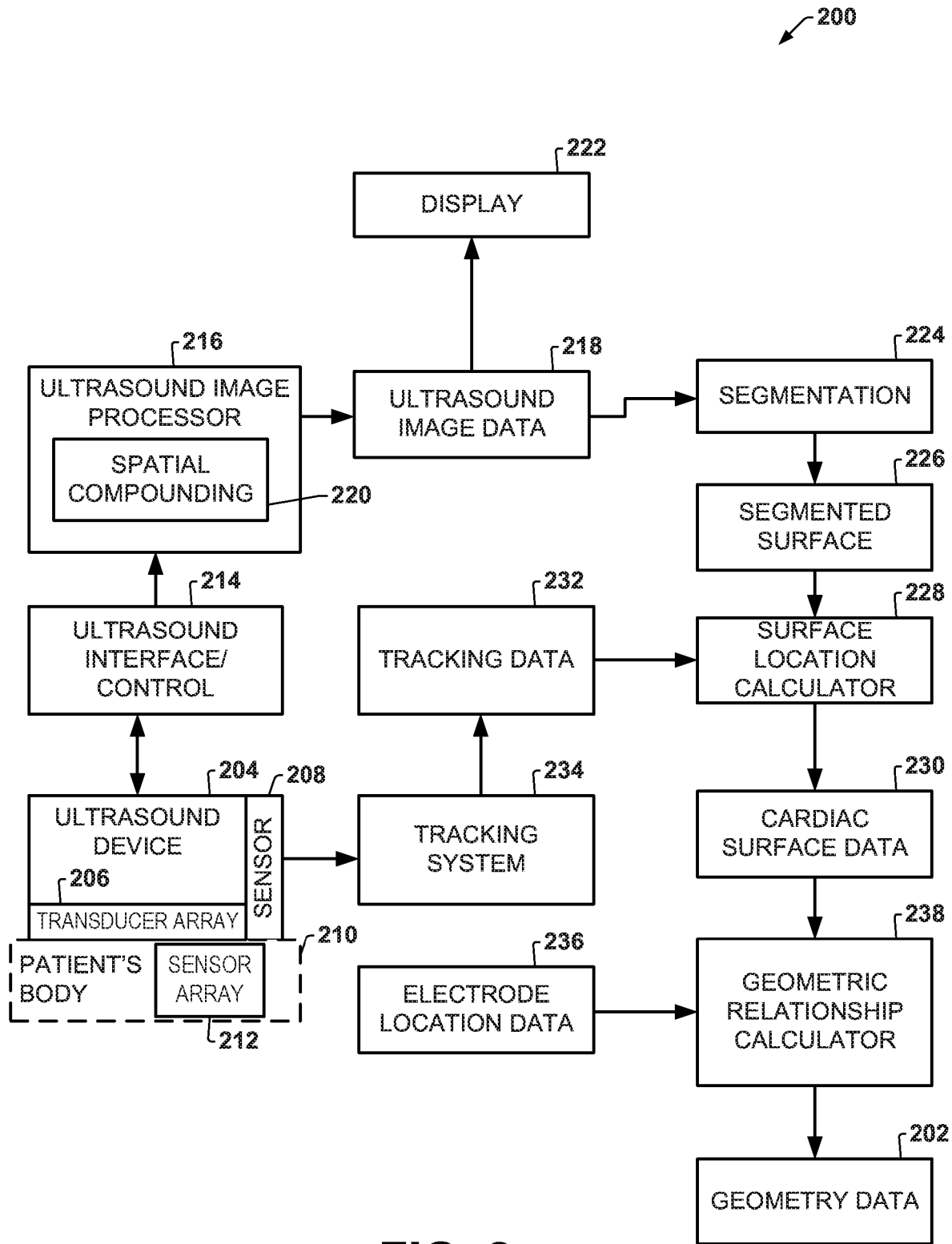
FIG. 2 is a block diagram depicting an example of a system to generate geometry data for cardiac mapping.
Figure 3:
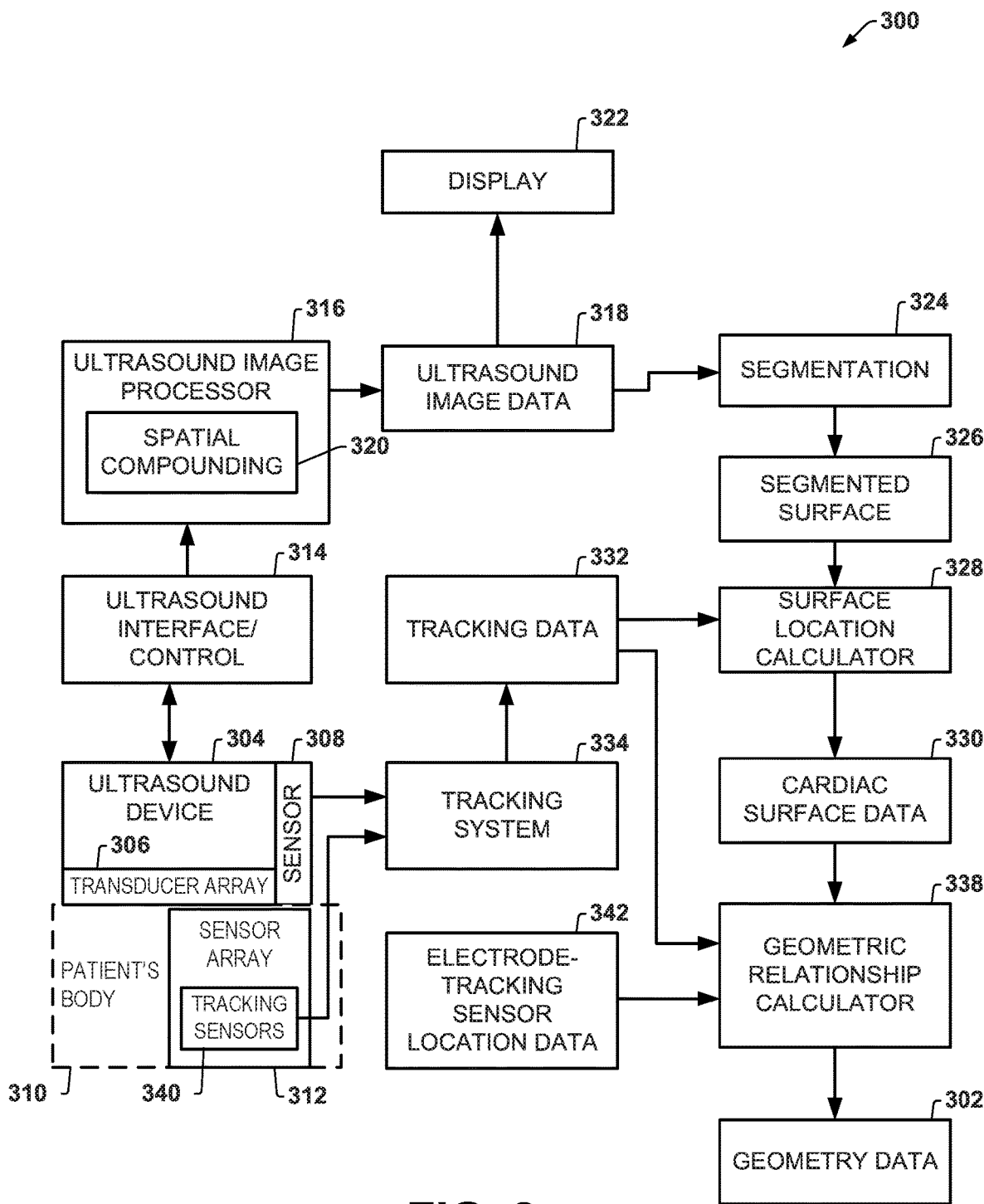
FIG. 3 is a block diagram depicting another example of a system to generate geometry data for cardiac mapping.

FIGS. 2 and 3 depict functional block diagrams of geometry determining systems that can be implemented. In each of the examples, the functional blocks represent data and functions or methods executable by one or more processors (e.g., processor 110) to perform the functions disclosed.

FIG. 2 depicts an example of a system 200 that can be utilized to generate geometry data 202 representing 3D spatial relationship between the cardiac surface and an arrangement of body surface electrodes (e.g., electrodes 106). The system 200 includes an ultrasound system comprising an ultrasound device 204, ultrasound interface/control and an ultrasound image processor 216. The ultrasound device 204 includes a transducer array 206. The ultrasound device 204 thus may perform scanning while in physical contact with the patient's skin (e.g., via an interface medium, such as a gel) to generate ultrasound images of the patient's body including the interior contents thereof.

As disclosed herein, the ultrasound device 204 includes one or more sensors 208 integrated into the device 204 to provide tracking information associated with the 3D location of the device. As demonstrated, a sensor array 212 is positioned on the patient's body 210. The sensor array can include an arrangement of electrodes distributed across the patient's outer body surface for measuring electrical activity (e.g., electrograms across the surface). Thus the ultrasound scans can be made while the sensor is positioned on the patient's body. In some cases, a portion of the sensor array 212 may be repositioned during ultrasound scanning or the ultrasound transducer may be integrated into the sensor array.

The ultrasound device 204 in turn provides signal to the ultrasound interface control module 214. The ultrasound interface/control 214 can process the signals from the device 204 for generating corresponding ultrasound image based upon the signals received. An ultrasound image processor 216 processes the image frames to generate ultrasound image data 218. For example, the ultrasound image processor 216 includes a spatial compounding function 220 to spatially correlate and compound the image frames provided by the ultrasound interface/control module 214. The ultrasound image data 218 can also be provided to a display 222 to visualize the current image being scanned by the device 204 and thereby provide guidance to the user for positioning the transducer array 206 with respect to the patient's body 210.

In some examples, the ultrasound image processor 216 can compute a confidence metric providing an indication of the completeness of the patient's heart as part of the data 218. The confidence metric may be presented as a value in the display or otherwise used to guide the user. For example, by displaying the compounded image over time, one or more portions that have not been imaged adequately may be visualized as an incomplete image, and the scanning angle of the ultrasound beam may be adjusted accordingly.

Based on the ultrasound image data 218, corresponding to a correlated and compounded image of the patient's body including the heart, a segmentation method 224 can be applied to the image. The segmentation provides a corresponding segmented surface 226 of the patient's heart. As an example, the segmentation can include thresholding and/or edge detection with respect to the ultrasound image to identify the cardiac surface(s) of interest.

A surface location calculator 228 can generate cardiac surface data 230 based on the segmented surface 226 of the heart and tracking data 232 representing the position and orientation of the ultrasound device 204 while it is provided by the sensor 208. For example, the sensor 208 can provide a corresponding sensor signal to a tracking system 234 that can convert the sensor signal to corresponding 3D position (e.g., spatial coordinates and orientation) corresponding to the tracking data 232. As mentioned, the tracking data can also be time stamped so as to time-correlate the position and orientation of the ultrasound device with respect to the image frames used to produce the ultrasound image 218. Thus the surface location calculator can compute the cardiac surface data representing the 3D coordinates of a plurality of points distributed across the surface corresponding to the segmented surface 226 in a corresponding coordinate system. The time correlation may also be used to enable gating of the image frames to one or more phases of the cardiac electrical cycle, as disclosed herein.

In the example of FIG. 2, the electrode location is specified by electrode location data 236. For example, the electrode location data 236 can be generated separately (different time and/or place) from the scanning and tracking implemented during such scanning. The electrode location data 236 can be in the same coordinate system as the cardiac surface data 230. In other examples, the electrode location data 236 can represent the position of each of the plurality of sensing electrodes in accordance system having a known relationship or a relationship that is ascertainable with respect to the cardiac surface data 230. A geometric relationship calculator 238 is programmed to compute the geometry data 202 based on the cardiac surface data 230 and the electrode location data 236. The geometry data thus expresses spatial locations of each of the plurality of body surface electrodes in a common three-dimensional coordinate system with a distribution of nodes across the cardiac surface.

FIG. 3 depicts an example of another system 300 that can be utilized to generate geometry data 302. In the example of FIG. 3, identical reference numbers increased by adding 100 are utilized to identify features previously introduced and described with respect to FIG. 2. Accordingly, reference may be made back to FIG. 2 and its description for additional information. The system 300 operates in a manner similar to that disclosed with respect to the system 200 of FIG. 2. However, the sensor array 312 includes an arrangement of tracking sensors 340 distributed on the sensor array. The tracking sensors 340 have a known position and orientation relative to the electrodes on the array. The relationship between the tracking sensors and the electrodes are described in electrode-tracking system location data 342, which can be stored in memory of the system 300. Thus, the electrode-tracking sensing location data 342 describes the relative geometry between the tracking sensors and respective electrodes in the sensor array 312.

Each of the tracking sensors 340 communicates tracking information to the tracking system 334 according to the tracking modality being utilized. For example, the tracking sensor 340 can provide an electric signal via an electric conductor to the tracking system 334 in response to an EM field generated by a field generator of the tracking system. Similarly, the ultrasound tracking sensor 308 provides tracking information to the tracking system 334 in response to the same field. Thus, the resulting tracking data 332 provided by the tracking system includes the 3D position (e.g., spatial coordinates) of each of the sensors 340 and 308 and, in some examples, also their orientation. Sensor data associated with the ultrasound device 304 are utilized by the surface location calculator 328 to generate the cardiac surface data 330 representing the plurality of points distributed across the cardiac surface (e.g., spatially correlated and compounded surface) in 3D space.

An electrode location calculator (not shown) determines the location of each of the electrodes in the sensor array 312 based on the tracking data 332 for the electrode tracking sensors 340 and the electrode-tracking sensor location data 342. The electrode calculator may be integrated as part of the geometric relationship calculator 338 or it could be a separate function that provides the electrode location data to the geometric relationship calculator 338. The resulting electrode location data for the electrodes thus can be similar to the data 236 of FIG. 2 and, in some examples, be in the same spatial coordinate system. The geometric relationship calculator 338 in turn computes the geometry data 302 based on the cardiac surface data 330 and the electrode location data, which is derived from the tracking data and the location data 342.

Figure 4:
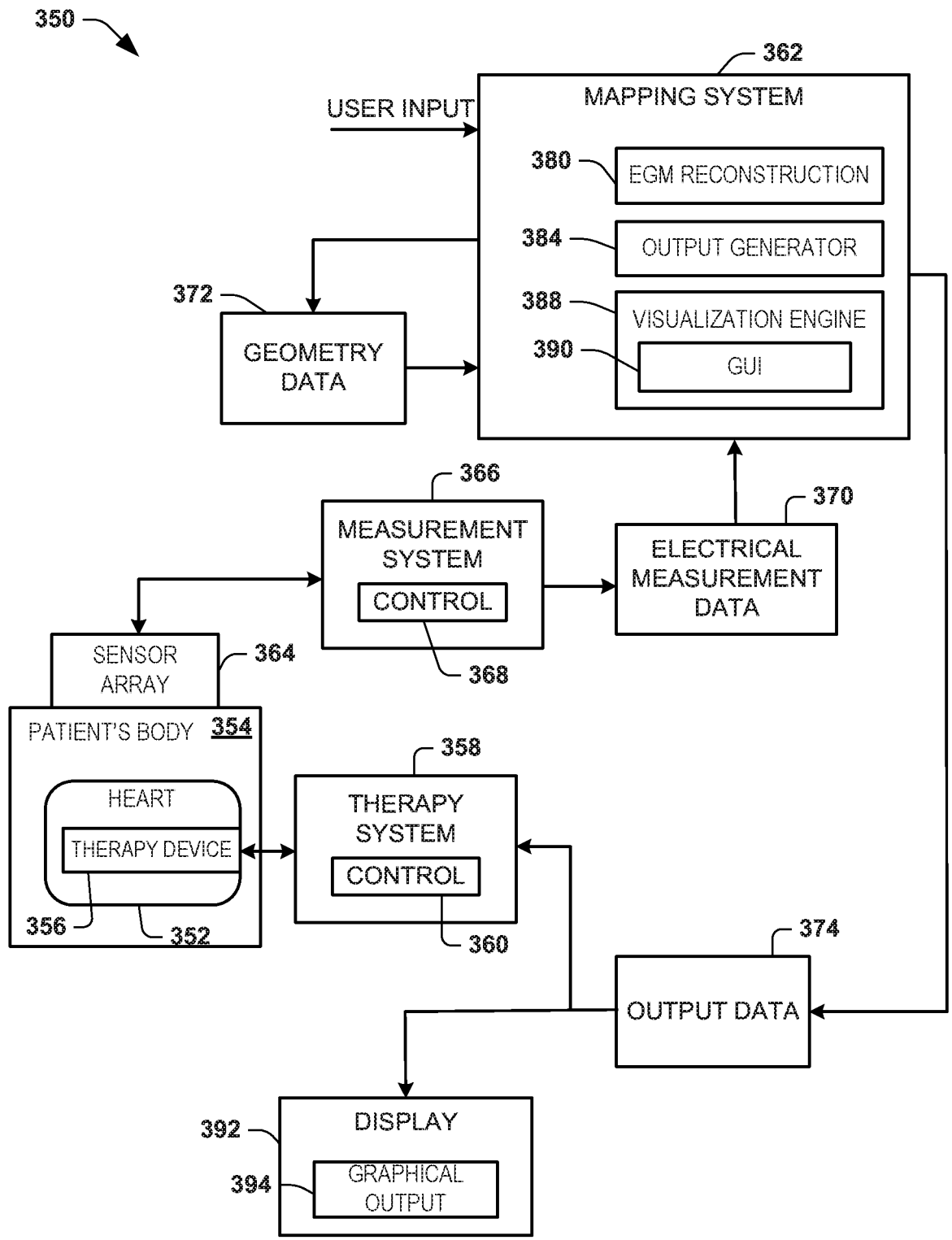
FIG. 4 depicts an example of a mapping and treatment system.

FIG. 4 depicts an example of a system 350 that can be utilized for performing medical testing (diagnostics, screening and/or monitoring) and/or treatment of a patient. In some examples, the system 350 can be implemented to generate corresponding maps for a patient's heart 352 in real time based on geometry data that is generated in a manner disclosed herein. Additionally or alternatively, the system 350 can be utilized as part of a treatment procedure, such as to help a physician determine parameters for delivering a therapy to the patient (e.g., delivery location, amount and type of therapy) based on one or more electrocardiographic maps that are generated.

As an example, a catheter having one or more therapy delivery devices 356 affixed thereto can be inserted into a patient's body 354 as to contact the patient's heart 352, endocardially or epicardially. The placement of the therapy delivery device 356 can be guided using the geometry data and information provided from one or more electroanatomic maps of the heart, such as disclosed herein. The guidance can be automated, semi-automated or be manually implemented based on information provided. Those skilled in the art will understand and appreciate various type and configurations of therapy delivery devices 356 that can be utilized, which can vary depending on the type of treatment and the procedure. For instance, the therapy device 356 can be configured to deliver electrical therapy (e.g., radiofrequency ablation or stimulation), chemical therapy, sound wave therapy, thermal therapy or any combination thereof. Other types of therapy can also be delivered via therapy system 358 and the invasive therapy delivery device 356 that is positioned within the body. The therapy system 358 and therapy device 356 may be omitted in some examples.

As a further example, the therapy system 358 can be located external to the patient's body 354 and be configured to control therapy that is being delivered by the device 356.

For instance, the therapy system 358 includes controls (e.g., hardware and/or software) 360 that can communicate (e.g., supply) electrical signals via a conductive link electrically connected between the delivery device (e.g., one or more electrodes) 356 and the therapy system 358. One or more sensors (not shown) can also communicate sensor information from the therapy device 356 back to the therapy system 358. The position of the device 356 relative to the heart 352 can be determined and tracked intraoperatively via a tracking modality and displayed via a mapping system 362, for example. The location of the device 356 and the therapy parameters thus can be combined to determine and control corresponding application of therapy. The functions of the mapping system 362 may be implemented as machine-readable instructions executable by one or more processors (e.g., processor 110).

In the example of FIG. 4, a sensor array 364 (e.g., corresponding to array 104, 212, 312) includes one or more electrodes that can be utilized for recording patient electrical activity. The sensing electrodes that form the array 364 can be mounted to a substrate (e.g., a wearable garment), be applied in strips of sensing electrodes or individually mounted electrodes. As one example, the sensor array 364 can correspond to a high-density arrangement of body surface sensors (e.g., greater than approximately 200 electrodes) that are distributed over a portion of the patient's torso for measuring electrical activity associated with the patient's heart (e.g., as part of an electrocardiographic mapping procedure). Some examples of a non-invasive sensor array that can be used are shown and described in the above incorporated U.S. Pat. No. 9,655,561, and International application No. PCT/US2009/063803. Other arrangements and numbers of sensing electrodes can be used as the sensor array 364. As an example, the array can be a reduced set of electrodes, which does not cover the patient's entire torso and is designed for measuring electrical activity for a particular purpose (e.g., an array of electrodes specially designed for analyzing atrial fibrillation and/or ventricular fibrillation) and/or for monitoring electrical activity for a predetermined spatial region of the heart (e.g., atrial region(s) or ventricular region(s)).

One or more sensors may also be located on the device 356 that is inserted into the patient's body. Such sensors can be utilized separately or in conjunction with the non-invasive sensors 364 for mapping electrical activity for an endocardial surface, such as the wall of a heart chamber, as well as for an epicardial surface.

In each of such example approaches for acquiring patient electrical information, including non-invasively or a combination of invasive and non-invasive sensing, the sensor array(s) 364 provide the sensed electrical information to a corresponding measurement system 366. The measurement system 366 can include appropriate controls and associated circuitry 368 for providing corresponding measurement data 370 that describes electrical activity detected by the sensors in the sensor array 364. The measurement data 370 can include analog and/or digital information (e.g., corresponding to electrical signals measured via sensor array 104, 212, 312).

The control 368 can also be configured to control the data acquisition process (e.g., sample rate, line filtering) for measuring electrical activity and providing the measurement data 370. In some examples, the control 368 can control acquisition of measurement data 370 separately from the therapy system operation, such as in response to a user input. In other examples, the measurement data 370 can be acquired concurrently with and in synchronization with delivering therapy by the therapy system, such as to detect electrical activity of the heart 352 that occurs in response to applying a given therapy (e.g., according to therapy parameters). For instance, appropriate time stamps can be utilized for indexing the temporal relationship between the respective measurement data 370 and therapy parameters use to deliver therapy as to facilitate the evaluation and analysis thereof.

The mapping system 362 is programmed to combine the measurement data 370 corresponding to electrical activity of the heart 352 with geometry data 372 by applying appropriate processing and computations to provide corresponding output data 374. The geometry data 372 may correspond to ultrasound-based geometry data, such as may be determined by device 108, data 202 or data 302 or by the methods of FIGS. 6 and 7 disclosed herein. The geometry data 372 thus represents a 3D geometric relationship between points on the cardiac surface and the electrodes positioned on the torso surface in a three-dimensional coordinate system. As an example, the output data 374 can include one or more graphical maps demonstrating determined arrhythmia drivers with respect to a geometric surface of the patient's heart 352 (e.g., information derived from electrical measurements superimposed on a surface of the heart 352).

Since the measurement system 366 can measure electrical activity of a predetermined region or the entire heart concurrently (e.g., where the sensor array 364 covers the entire thorax of the patient's body 354), the resulting output data (e.g., visualizing attributes of identified stable rotors and/or other electrocardiographic maps) 374 thus can also represent concurrent data for the predetermined region or the entire heart in a temporally and spatially consistent manner. The time interval for which the output data/maps are computed can be selected based on user input (e.g., selecting a timer interval from one or more waveforms). Additionally or alternatively, the selected intervals can be synchronized with the application of therapy by the therapy system 358.

For example, electrogram reconstruction 380 can be programmed to compute an inverse solution and provide corresponding reconstructed electrograms based on the electrical measurement data 370 and the geometry data 372. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be implemented by electrogram reconstruction 380 include those disclosed in U.S. Pat. Nos. 7,983,743 and 6,772,004. The EGM reconstruction 380 thus can reconstruct the body surface electrical activity measured via the sensor array 364 onto a multitude of locations on a cardiac envelope (e.g., greater than 1000 locations, such as about 2000 locations or more. For example, the locations may be nodes distributed across a mesh model (e.g., corresponding to the points defined by cardiac surface data 230, 330) derived from ultrasound image data and tracking data, as disclosed herein.

As disclosed herein, the cardiac envelope can correspond to a 3D surface geometry corresponding to the heart, which surface can be epicardial and/or endocardial surface model derived at least in part from ultrasound image data. Additionally, the geometry data 372 that is utilized by the electrogram reconstruction 380 can correspond to actual patient anatomical geometry, a preprogrammed generic model or a combination thereof (e.g., a model/template that is modified based on patient anatomy), such as based on ultrasound image data as disclosed herein.

As mentioned above, the geometry data 372 can correspond to a mathematical model that has been constructed based on ultrasound image data for the patient. Appropriate anatomical or other landmarks, including locations for the electrodes in the sensor array 364 can be identified in the geometry data 372 to facilitate registration of the electrical measurement data 370 and performing the inverse method thereon. The identification of such landmarks can be done manually (e.g., by a person via image editing software) or automatically (e.g., via image processing techniques). By way of further example, the ultrasound imaging and generation of the geometry data 372 may be performed concurrently with recording the electrical activity that is utilized to generate the electrical measurement data 370. In another example, the ultrasound imaging can be performed separately (e.g., before or after the measurement data has been acquired) from the electrical measurements.

Following (or concurrently with) determining electrical potential data (e.g., electrogram data computed from non-invasively or from both non-invasively and invasively acquired measurements) across the geometric surface of the heart 352, the electrogram data can further undergo signal processing by mapping system 362 to generate the output data 374, which may include one or more graphical maps of cardiac electrical activity or derivations thereof. The mapping system 362 can include one or more methods programmed to characterize the electrical information across the cardiac envelope.

An output generator 384 can be programmed to generate one or more graphical outputs (e.g., waveforms, electroanatomic maps or the like) for display based on the output data 374. A visualization engine 388 can control features of the output being displayed. For instance, parameters associated with the displayed graphical output, corresponding to an output visualization of a computed map or waveform, such as including selecting a time interval, temporal and spatial thresholds, as well as the type of information that is to be presented in the display 392 and the like can be selected in response to a user input via a graphical user interface (GUI) 390. For example, a user can employ the GUI 390 to selectively program one or more parameters (e.g., temporal and spatial thresholds, filter parameters and the like) utilized by the one or more methods used to process the electrical measurement data 370. The mapping system 362 can generate corresponding output data 374 that can in turn be rendered as a corresponding graphical output in a display 392, such as including one or more graphical visualizations 394. For example, the output generator 384 can generate maps and other output visualizations.

Additionally, in some examples, the output data 374 can be utilized by the therapy system 358. For instance, the control system 360 may implement fully automated control, semi-automated control (partially automated and responsive to a user input) or manual control based on the output data 374. In some examples, the control 360 of the therapy system 358 can utilize the output data 374 to control one or more therapy parameters. As an example, the control 360 can control delivery of ablation therapy to a site of the heart (e.g., epicardial or endocardial wall) based on one or more arrhythmia drivers identified by one or more method(s). In other examples, an individual can view the map generated in the display to manually control the therapy system. Other types of therapy and devices can also be controlled based on the output data 374 and corresponding graphical map 394 presented on the display 392.

Figure 5:
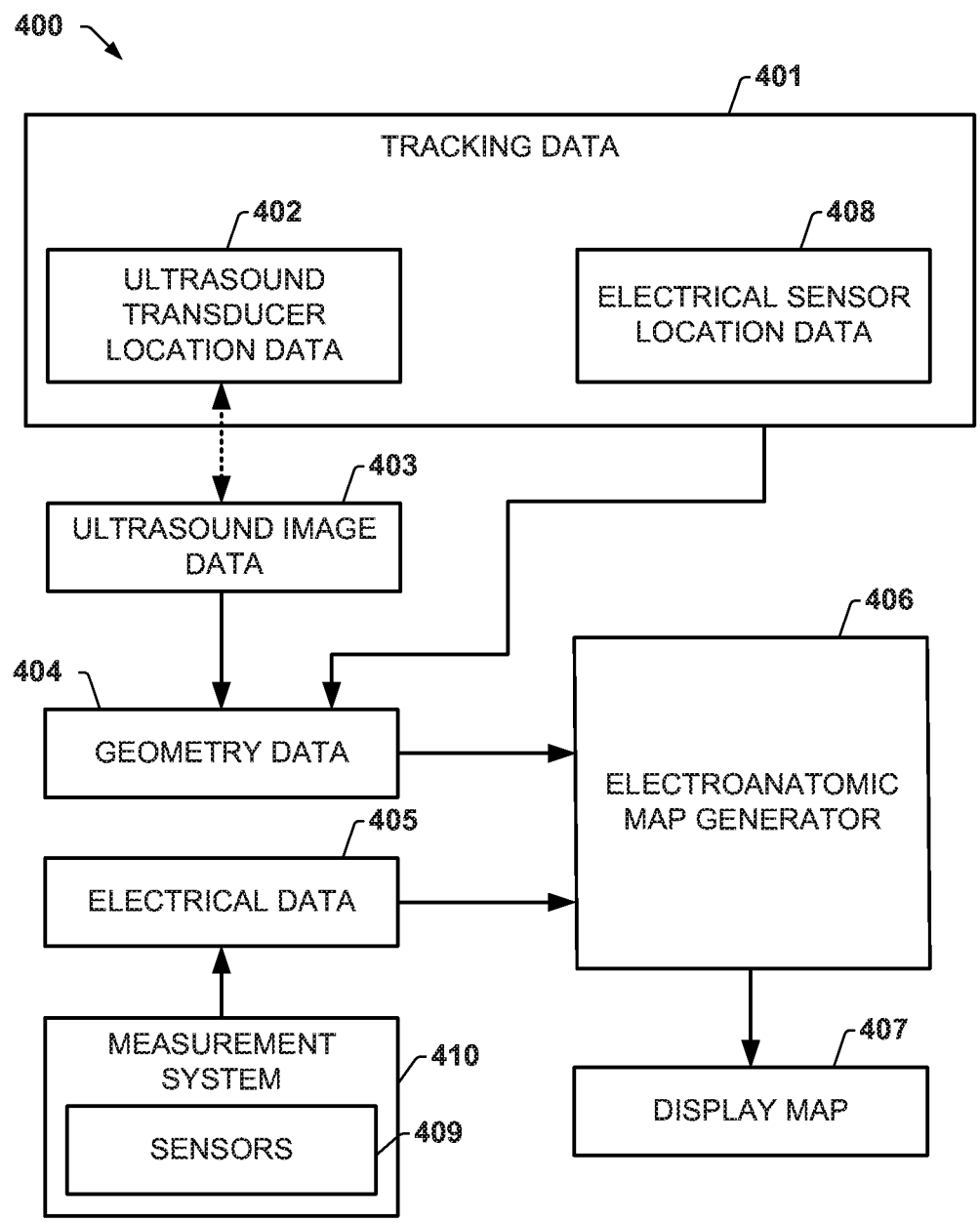
FIG. 5 depicts an example of another system for cardiac mapping based on geometry data determined.

FIG. 5 shows an example of another system 400 for cardiac mapping (e.g., electrocardiographic imaging (ECGI)) using the ultrasound based geometry determination. The cardiac map is just one example of an electroanatomic map that can be generated as a display map 407 by the system 400. Similar to the system of FIG. 4, the system 400 can generate and display a map 407 based on patient geometry data 404, as determined based on the ultrasound based geometry determination, and electrical data 405, recorded by the body surface electrodes. The geometry data 404 can be embodied as a model that can be generated and updated during ultrasound imaging. As an example, the geometry data 404 can correspond to a surface model of a patient's entire organ, such as the heart, or a portion of the entire organ, which can be graphically rendered as a two- or three-dimensional representation in the display map 407. The model, for example, can be created using shape constraints that force the model to retain a general heart shape, thus preventing the model from adapting itself into unrealistic geometry. The general heart shape, corresponding to a cardiac surface derived from ultrasound image and tracking data, can be refined and/or validated based on images from another imaging modality (e.g., MRI or CT images of the heart either from the patient himself or from other patients) or a generic heart model.

The display map 407 can be determined based on geometry data 404 and electrical data 405. The geometry data 404 can be based on a compounded volume that is determined based on a plurality of ultrasound images 403. The ultrasound images 403 can be 2D (b-mode) slices or 4D volumes. The compounding of the ultrasound images 403 can lead to an improved signal to noise ratio. As an example, gating of the acquisition can facilitate compounding the ultrasound images 403 at the same phase of the cardiac cycle.

The geometry data 404 is provided based on the compounded ultrasound image 406 and tracking data 401. In this example, the tracking data 401 includes ultrasound transducer location data 402 and electrode location data 408. The ultrasound transducer location data 402 is related to the location and orientation of an ultrasound transducer (e.g., transducer 102, 206, 306) during scanning. The data 402 thus represents the location of the transducer in 3D space that is used to generate the ultrasound image data 403. The tracking data 401 also includes electrode location data representing the 3D location of the sensors 409 in the same coordinate system as the transducer coordinates.

Model based segmentation can be applied to the ultrasound image data (e.g., spatially compounded image) for deriving a heart surface mesh. In some examples, a user conducting the test can select reference points on the ultrasound images 403 which can be correlated to transducer location data 402 to ascertain coordinates in 3D space. As another example, the system 400 can automatically segment and register points on the mesh with respect to the transducer location data 402. This segmentation can begin early in acquisition and as more data is acquired, segmentation can automatically refine as additional ultrasound image frames are acquired over time.

By way of example, the ultrasound transducer location data 402 can include position and orientation recorded by one or more six-degree of freedom sensors attached to the ultrasound transducer. The six-degree of freedom sensor permits tracking of the transducer location and orientation and enables for time-based correlation between acquired images for compounding. The electrical sensor location data 408 can be related to a set of tracking elements having a known position with respect to electrical sensors 409 (part of electrical measurement system 410) that are used to measure electrical activity across the body surface. The electrical sensor location data 408 thus is used to determine location of the electrical sensors (electrodes) 409 of measurement system 410 and provide corresponding geometry data 404 for the electrodes registered in a common coordinate system as the ultrasound image space and the heart surface model. The measurement system 410 can employ signal processing (e.g., filters, channel integrity detection) for signals provided via input channels from each of the sensors 409.

The sensors 409 can measure electrical signals, which can be digitized at a sample rate and stored as the electrical data 405 in memory with the geometry data 404. The electroanatomic map generator 406 includes instructions (executable by a processor) to combine the electrical data 405 with the geometry data 404 to determine the display map 407. The electroanatomic map generator 406 can be programmed to implement an inverse method, which relates the electrical data 405, recorded on the body surface, to the geometry data 404, corresponding to the geometry of the heart. Examples of the inverse method that can be implemented by the electroanatomic map generator 406 to reconstruct electrograms on a cardiac envelope (cardiac surface) from the electrical data 405 and geometry data 404 include those disclosed in U.S. Pat. Nos. 7,983,743 and 6,772,004. This and other techniques to solve the inverse problem can generate electrophysiological data by combining body surface electrical measurements with patient geometry information. Thus, the electroanatomic map generator uses the results of the inverse method to provide the corresponding electrical data 405 that is registered with the patient geometry data 404, thereby providing electrical potentials concurrently for each of a plurality of points on the cardiac envelope (heart surface).

As mentioned above, the measurement locations corresponding to the electrical data 405 can be registered into a common coordinate system with the patient geometry data 404 and provided the tracking data 401. For example, the electrical data 405 can be stored in a data structure of rows (corresponding to different spatial locations for each input channel) and columns (corresponding to samples) in which the rows of data have the same index as (or are registered to) respective points residing on patient geometry data 404. This registration or indexed relationship between the electrical data 405 and the patient geometry data 404 is indicated by a dashed line between the ultrasound transducer location data 402 and the electrical sensor location data 408. In one example, the samples in each of the columns can represent simultaneous information across the entire surface region (e.g., the heart) of the patient.

Figure 6:
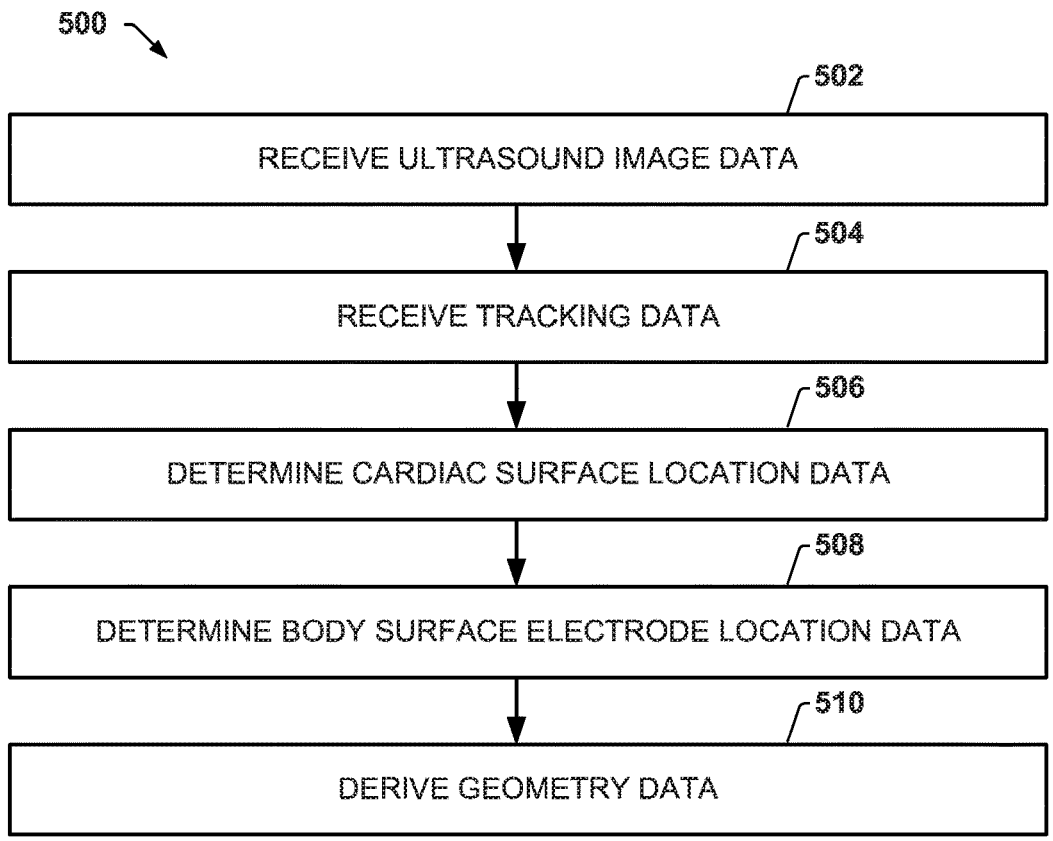
FIG. 6 is a flow diagram illustrating an example of a method that can be used to acquire the geometry of the surface of the heart.
Figure 7:
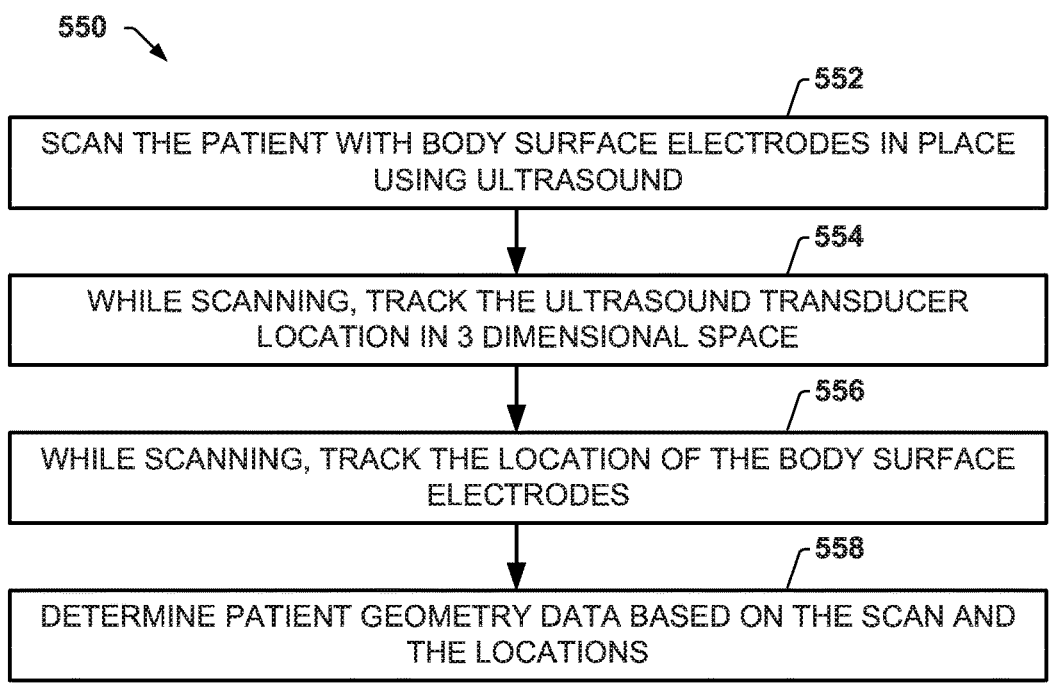
FIG. 7 is a flow diagram illustrating an example of a method that can be used to acquire the geometry of the surface of the heart.

In view of the foregoing structural and functional features described above, methods that can be implemented will be better appreciated with reference to FIGS. 6 and 7. While, for purposes of simplicity of explanation, the methods are shown and described as executing serially, it is to be understood and appreciated that the present invention is not limited by the illustrated order, as some aspects could occur in different orders and/or concurrently from that shown and described herein. Moreover, not all illustrated features may be required to implement a method. The methods or executable portions thereof can be implemented as instructions stored in a non-transitory storage medium and be executed by a processor of a computer device or special purpose computer device (e.g., a dedicated computer or workstation) to access data sources and perform the functions disclosed herein, for example.

FIG. 6 depicts an example method 500, such as may be implemented via the systems of FIG. 1, 2 or 3, which can include one or more processors and memory (local and/or remote). The method begins at 502 by receiving ultrasound image data. As disclosed herein, the image data may be generated by an ultrasound device as an ultrasound transducer scans a patient's body that includes a plurality of body surface electrodes positioned at known relative positions. The ultrasound image data includes one or more ultrasound images (image frames) of the patient's heart. In some examples, the ultrasound image data is a compound image that includes at least a portion of the patient's heart. For example, a plurality of ultrasound image frames are spatially compounded to generate the compounded image.

At 504, tracking data is received. The tracking data may be generated based on a tracking signal from one or more tracking sensor associated with (e.g., attached to an ultrasound) the ultrasound probe carrying the transducer. The tracking data represents location of the ultrasound transducer in 3D space over time as an ultrasound transducer scans the patient's body. For example, the tracking data is generated by a tracking system (e.g., 108, 234, 334) based on tracking sensor signals to provide both position and orientation of each respective tracking sensor and the object to which it is affixed.

In some examples, the tracking data received at 504 is provided based on tracking signals from electrode tracking sensors such that the tracking data further represents locations of the electrode tracking sensors in the three dimensional space. For example, the location of each of the electrode tracking sensor has a predetermined (known) relative position with respect to at least some of the plurality of body surface electrodes. Thus, the 3D spatial location of each of the body surface electrodes can be determined in based on the locations of the electrode tracking sensors represented by the tracking data and the electrode relative position data describing the known relative positions of the plurality of body surface electrodes with respect to each other and to the tracking sensors. As mentioned, the electrode tracking sensors may be aligned with or co-located with respect to a center of a respective one of the plurality of electrodes.

At 506, the method 500 includes determining cardiac surface location data representing spatial locations (e.g., 3D coordinates) along a surface of the patient's heart based on the tracking data and the ultrasound image data. For example, the compounded ultrasound image is segmented to identify the surface of the patient's heart in the compound image. A surface model of the patient's heart can be generated based on the segmented image, such that the locations on the surface of the patient's heart correspond to a plurality of points distributed across the surface model of the patient's heart. As a further example, surface corresponds to an epicardial surface mesh of the patient's heart that is generated based on the segmented image. The nodes of the mesh thus represent points distributed across the surface of the patient's heart onto which corresponding electrical signals are to be reconstructed.

At 508, electrode location data is determined. The electrode location data represents the locations of the plurality of body surface electrodes in the 3D space. As disclosed herein, the electrode locations can be determined according to a process performed separately (in time) from the ultrasound image scanning that is used to derive the ultrasound image data at 502. For example, a laser digitizer can be used to ascertain the relative 3D position of the electrodes. In some examples, an arrangement of tracking sensors are positioned at a known spatial relationship (and orientation) with respect to some of the electrodes, such that electrode tracking data can be used to register the electrode tracking sensors and the associated electrodes into a common coordinate system with the cardiac surface data. The electrode location data thus may be computed based on the locations of the electrode tracking sensors, as represented by the tracking data, and the electrode relative position data describing the known relative positions of the plurality of body surface electrodes and tracking sensors. The number of electrode tracking sensors and their positions with respect to electrodes can be set according to the number of electrodes and their distribution across the patient's body.

At 510, geometry data is derived based on the electrode location data and the cardiac surface data. The geometry data thus represents a geometric relationship (e.g., in 3D space) between the locations of the plurality of body surface electrodes and locations (e.g., nodes) along the surface of the patient's heart represented by the cardiac surface data. As disclosed herein, electrical signals can be measured non-invasively with the body surface electrodes and corresponding electrical signals can be reconstructed onto the cardiac surface based on the measured signals and the geometry data.

FIG. 7 depicts another example of a method 550 to generate geometry data corresponding to a geometric relationship between a model of the heart surface and sensing electrodes in a common 3D coordinate system. While the method 550 of FIG. 7 is described in the context of the system 100 of FIG. 1, such that reference is made back to FIG. 1, the method is applicable to other system configurations, such as disclosed herein.

At 552, ultrasound images can be acquired (e.g., by ultrasound transducer 102) while the patient is wearing the sensor array 104. While scanning, at 554, the location of the ultrasound transducer 102 can be tracked in 3D space. For example, the tracking sensor 116 is attached to the ultrasound transducer 102 and tracking system 114 provides corresponding tracking data representing the location of the transducer over time during the scanning at 552 in 3D space, such that one or more image volumes can be generated with real world coordinates. As an example, the ultrasound tracking sensor 116 can include a five- or six-degree of freedom sensor coil attached to the ultrasound transducer 102 that tracks location and orientation thereof for the transducer to which it is attached. The tracking system 108 thus provides position and orientation information for the ultrasound transducer 102 over time that enables correlation between acquired images for compounding. Time correlation between cardiac cycles may also be provided as disclosed herein.

As an example, the geometry of the heart surface can be represented as a mesh of the heart surface. The spatial geometry of the heart surface can be determined based on correlated and compounded ultrasound images and the location of the ultrasound transducer 102 (from tracking system 114). The geometry of the heart surface can be derived from the image based on a model-based segmentation procedure, which can be automatic and/or manual, based on one or more reference points identified on one or more of the ultrasound images. The reference points can include anatomical landmarks, such as disclosed herein. Additionally or alternatively, the heart may be segmented based on long and short axes of the heart.

Also during ultrasound scanning, at 556, the location of electrodes 106 in the sensor array 104 can be tracked (by tracking system 108). For example, the location of electrodes 106 may be tracked according to the location of an electrode tracking modality (e.g., tracking sensors 118) having a known position with respect to the electrodes. By using the same tracking system 114 for localizing both the transducer 102 and the electrodes 106, in some examples, the spatial position of the electrodes thus can be determined in the same coordinate system as the image volume. As a result, each electrode location is known relative to the acquired image volume (a compounded image). In other examples, a different tracking modality from the sensor 116 can be used for tracking the electrodes, although registration into a common coordinate system with the image volume (and cardiac surface model) will be needed.

As an example, the electrode tracking modality 118 can include a plurality of tracking elements embedded or attached to the sensors of sensor array 104. For example, the tracking employs at least two tracking sensors 118, such as six-degree of freedom sensors, having a known location at (fixed to) or relative the sensors. The tracking system 114 can include any number of tracking elements, such as sufficient to determine positions of sensors distributed across the patient's body surface. The tracking system 108 can provide tracking data corresponding to the location and orientation of the modality on the body surface. For instance, the sensor tracking modality 118 can include fewer tracking elements than electrodes, and the location of other sensors between the tracking elements can be interpolated based on a known geometry of the sensors with respect to the tracking elements. Additionally or alternatively, the ultrasound transducer 102 and its associated tracking sensor 116 can be used as a pointing device for additional sensor and/or electrode location information. The tracking system 114 can also reduce the effects of any patient movement by providing position information associated with movement of individual sensors in the sensor system 104.

At 558, patient geometry data is determined based on the locations of the ultrasound transducer 102 and the body surface electrodes 106. The geometry data can include locations of the body surface electrodes on the surface of the patient's body as well as location of points on an internal anatomical surface of interest (cardiac surface, such as the epicardium). For example, the geometry data can be generated as one or more models that are updated as the imaging and tracking occurs.

As an example, the geometry data can correspond to a 3D surface model for electrode locations on the patient's torso and another 3D surface model of a patient's entire organ, such as the heart, or a portion of the entire organ (e.g., a contour surface mesh). The heart surface model, which is derived from the ultrasound image data, can be refined and/or validated based on MRI or CT images of the heart either from the patient himself (from another procedure at a different time), from other patients or a generic heart model. Alternatively, a coarse heart model may be generated from image data acquired via another modality (e.g., X-ray, MRI and/or CT), and the ultrasound image acquisition and processing thereof may guide adaptation of the heart model or facilitate registration with the electrode geometry.

In view of the foregoing structural and functional description, those skilled in the art will appreciate that portions of the invention may be embodied as a method, data processing system, or computer program product. Accordingly, these portions of the present invention (e.g., computing device 106) may take the form of an entirely hardware embodiment, an entirely software embodiment, or an embodiment combining software and hardware, such as shown and described. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means "based at least in part on."

What is claimed is:

1. A system comprising:
a plurality of body surface electrodes adapted to be placed on an outer surface of a body surface of a patient to measure cardiac electrical activity from the body surface;
one or more non-transitory machine readable media to store data and instructions; and
a processor to access the media and execute the instructions to at least:
access ultrasound image data comprising a plurality of ultrasound image frames that includes a heart of the patient;
determine locations of an ultrasound transducer, which provides the ultrasound image data, and the plurality of body surface electrodes in a three-dimensional coordinate space based on tracking data, the tracking data representing a position of at least one ultrasound tracking sensor and representing a position of at least one electrode tracking sensor as the ultrasound transducer scans the patient's body;
determine locations of the plurality of body surface electrodes in the three-dimensional coordinate space based on the tracking data received from the at least one electrode tracking sensor;
determine cardiac surface data to represent locations on a cardiac envelope based on the tracking data, which represents the position of the at least one ultrasound tracking sensor, and the ultrasound image data; and
derive geometry data to represent a geometric relationship between the position of the plurality of body surface electrodes and the locations on the cardiac envelope represented by the cardiac surface data.

2. The system of claim 1, wherein the instructions are further to:
select ultrasound image frames from the ultrasound image data that are gated with respect to a given phase of a cardiac cycle of the patient's heart; and
compound the selected ultrasound images frames gated with respect to the given phase of the cardiac cycle to provide compounded image data for the given phase, wherein the geometry data represents the geometric relationship between the position of the plurality of body surface electrodes and the locations on the cardiac envelope for the given phase of the cardiac cycle.

3. The system of claim 1, wherein the instructions are further to:
select ultrasound image frames from the ultrasound image data that are gated with respect to multiple phases of a cardiac cycle of the patient's heart; and
compound the selected ultrasound images frames for each of different phases of the cardiac cycle to provide respective compounded image data for each of the phases of the cardiac cycle, wherein the geometry data is derived based on the respective compounded image data for each of the phases of the cardiac cycle to represent the geometric relationship between the position of the plurality of body surface electrodes and the locations on the cardiac envelope for the each of the phases of the cardiac cycle.

4. The system of claim 3, wherein the instructions are further to:
determine the cardiac surface data to represent corresponding locations on the cardiac envelope at each of the phases of the cardiac cycle based on the tracking data and the ultrasound image data that are gated to the cardiac cycle based on a time correlation thereof; and
generate a multiphase model of the cardiac envelope that represents geometry of the cardiac envelope for each respective phase of the cardiac cycle based on the cardiac surface data determined for each respective phase.

5. The system of claim 4, wherein the ultrasound image data and the tracking data are acquired over a plurality of cardiac cycles,
wherein the instructions to generate the multiphase model further comprise instructions to:
segment the compounded image data acquired for each of the phases over the plurality of cardiac cycles to provide segmented image data identifying the locations on the cardiac envelope for each of the respective phases of the cardiac cycle.

6. The system of claim 4, wherein the cardiac electrical activity measured by the electrodes is stored in the media as electrical data having a known time correlation with respect to the tracking data and the ultrasound data, wherein the wherein the instructions are further to:

map the electrical data, which represents the cardiac electrical activity measured by the electrodes, to each respective phase of the multiphase model of the cardiac envelope based on the time correlation.

7. The system of claim 1, wherein the instructions are further to:
segment the ultrasound image data that is acquired during scanning of the patient's body to identify the locations on the cardiac envelope; and
generate feedback during the scanning based on the segmenting, the feedback including an indication of completeness of the ultrasound image data for patients heart.

8. The system of claim 7, wherein the instructions to generate the feedback are further to:
compute a confidence metric having a value representing the indication of completeness of the ultrasound image data for the patients heart, the feedback being provided based on the value of the computed confidence metric.

9. The system of claim 1, further comprising a tracking system in communication with a plurality of tracking sensors, the plurality of tracking sensors comprising at least one ultrasound tracking sensor associated with the ultrasound transducer and at least one electrode tracking sensor having a predetermined position with respect to at least some of the plurality of body surface electrodes, the tracking system to provide the tracking data.

10. The system of claim 9, wherein the plurality of tracking sensors comprise a magnetic sensor, an electromagnetic sensor, or an optical sensor.

11. The system of claim 1, wherein the geometry data comprises a first three-dimensional surface model for electrode locations on the patient's body and a second three-dimensional surface model for the locations on the cardiac envelope.

12. The system of claim 1, wherein the ultrasound image data comprises a plurality of two-dimensional ultrasound images or a plurality of three-dimensional ultrasound images, which are correlated and compounded together to create an ultrasound image volume representing at least a portion of the patient's heart.

13. The system of claim 1, wherein the tracking data includes position information associated with movement of the electrodes on the body surface, and the instructions are further to reduce effects of patient movement in the geometry data based on the movement of electrodes reflected in the tracking data.

14. One or more non-transitory media that stores instructions, which when executed by a processor, cause the processor to perform a method that comprises:
accessing ultrasound image data comprising a plurality of ultrasound image frames that includes a patient's heart;
determining locations of an ultrasound transducer, which provides the ultrasound image data, and a plurality of body surface electrodes in a three-dimensional coordinate space based on tracking data, the tracking data representing a position of at least one ultrasound tracking sensor and representing a position of at least one electrode tracking sensor as the ultrasound transducer scans the patient's body;
determining electrode position data, which represents locations of the plurality of body surface electrodes in the three-dimensional coordinate space, based on the tracking data received from the at least one electrode tracking sensor;

determining cardiac surface data, which represents locations on a cardiac envelope, based on the tracking data representing the position of the at least one ultrasound tracking sensor and the ultrasound image data; and
deriving geometry data, which represents a geometric relationship between the position of the plurality of body surface electrodes and the locations on the cardiac envelope, based on the electrode position data and the cardiac surface data.

15. The media of claim 14, wherein the method further comprises:
selecting ultrasound image frames from the ultrasound image data that are gated with respect to a given phase of a cardiac cycle of the patient's heart; and
compound the selected ultrasound images frames to provide compounded image data for the given phase, wherein the geometry data represents the geometric relationship between the position of the plurality of body surface electrodes and the locations on the cardiac envelope for the given phase of the cardiac cycle.

16. The media of claim 14, wherein the method further comprises:
selecting ultrasound image frames from the ultrasound image data that are gated with respect to multiple phases of a cardiac cycle of the patient's heart; and
compounding the ultrasound images frames selected for each of the phases of the cardiac cycle to provide respective compounded image data for each of the respective phases of the cardiac cycle, wherein the geometry data is derived based on the respective compounded image data for each of the phases of the cardiac cycle to provide a multiphase model that includes a plurality of phase models representing the geometric relationship between the position of the plurality of body surface electrodes and the locations on the cardiac envelope for each respective phase of the cardiac cycle.

17. The media of claim 14, wherein the method further comprises:
mapping electrical data, which represents cardiac electrical activity measured by the electrodes on a surface of the patient's body, to each respective phase model of the multiphase model based on a known time correlation between the electrical data, the tracking data and the ultrasound data.

18. The media of claim 14, wherein the method further comprises:
segmenting the ultrasound image data that is acquired during scanning of the patient's body to identify the locations on the cardiac envelope; and
generating feedback during the scanning based on the segmenting, the feedback including an indication of completeness of the ultrasound image data for patients heart.

19. The media of claim 14, wherein the ultrasound image data comprises a plurality of two-dimensional ultrasound images or a plurality of three-dimensional ultrasound images, which are correlated and compounded together to create an ultrasound image volume representing at least a portion of the patient's heart.

20. The media of claim 14, wherein the method further comprises:
reducing effects of patient movement in the geometry data based on the tracking data reflecting movement of electrodes on a surface the patient's body.

* * * * *